United States Patent [19]

Ness et al.

[11] Patent Number: 5,016,466
[45] Date of Patent: May 21, 1991

[54] TEST APPARATUS AND METHOD FOR BLOOD PRESSURE MEASURING EQUIPMENT

[76] Inventors: Dale C. Ness, 4601 E. 16th, Tucson, Ariz. 85711; Dirk B. Call, 6709 Half Moon Pl., Tucson, Ariz. 85741

[21] Appl. No.: 427,475

[22] Filed: Oct. 27, 1989

[51] Int. Cl.⁵ .............................................. G01L 27/00
[52] U.S. Cl. .................................... 73/4 R; 434/262; 434/267
[58] Field of Search ............. 73/4 R, 4 V, 4 D, 866.4; 434/262, 267, 268; 128/672, 681; 606/202; 623/1, 57

[56] References Cited

U.S. PATENT DOCUMENTS

| | | | |
|---|---|---|---|
| 2,556,043 | 6/1951 | Roucka | 35/17 |
| 2,976,715 | 3/1961 | Reese et al. | 73/4 R |
| 2,995,832 | 8/1961 | Alderson | 35/17 |
| 3,376,660 | 4/1968 | McGinnis | 434/268 |
| 3,552,036 | 1/1911 | Mahler | 434/262 |
| 3,662,076 | 5/1972 | Gordon et al. | 434/267 X |
| 3,868,844 | 3/1975 | Klien | 73/4 R |
| 4,182,054 | 1/1980 | Wise et al. | 35/17 |
| 4,269,058 | 5/1981 | Richman | 73/4 R |
| 4,342,218 | 8/1982 | Fox | 73/4 R |
| 4,372,148 | 2/1983 | Cieutat | 73/4 R |
| 4,464,123 | 8/1984 | Glover et al. | 73/4 R X |
| 4,873,989 | 10/1989 | Djordjevich et al. | 128/681 X |

FOREIGN PATENT DOCUMENTS

| | | | |
|---|---|---|---|
| 3602171 | 7/1987 | Fed. Rep. of Germany | 434/267 |
| 103442 | 8/1980 | Japan | 73/4 R |
| 632351 | 9/1982 | Switzerland | 434/267 |
| 823918 | 4/1981 | U.S.S.R. | 73/4 R |

Primary Examiner—Tom Noland
Attorney, Agent, or Firm—Victor Flores

[57] ABSTRACT

The present invention discloses apparatus and method for testing and verifying the accuracy of non-invasive and invasive blood pressure measuring equipment. The apparatus includes pneumatic and electronic components that simulate the delivery of systolic and diastolic pressures to a mock human member and further includes a monitoring portion for displaying the response of the blood pressure measuring equipment under test.

13 Claims, 4 Drawing Sheets

TEST APPARATUS AND METHOD FOR BLOOD PRESSURE MEASURING EQUIPMENT

FIELD OF THE INVENTION

This invention relates to apparatus and method used for testing and verifying the accuracy of blood pressure measuring equipment. More particularly, the present invention relates to apparatus and method that test and verify the accuracy of noninvasive and invasive blood pressure measuring equipment. Even more particularly, the present invention relates to apparatus and method used for testing and verifying the accuracy of blood pressure measuring equipment using pneumatic and electronic wave shaping equipment that simulate the delivery of systolic and diastolic blood pressures of a human to a mock human member and that further include monitoring the response of the blood pressure measuring equipment under test.

DESCRIPTION OF THE PRIOR ART

Blood pressure measurement equipment are well known and are typically categorized as either invasive or non-invasive types. The non-invasive blood pressure measuring equipment typically include an arm cuff member coupled at one end to pressure sensitive instrumentation. The cuff member senses pressure variations in a human and transmits the variations to the instrumentation that generates equivalent blood pressure reading.

Known prior art in the field of verification test systems for blood pressure measuring equipment includes U.S. Pat. No. 3,868,844 which teaches a driven cam means in a pressure chamber that displaces a flexible member within the chamber that produces variable pressure that simulates a hypothetical arterial blood pressure cycle and that is used for verifying and calibrating direct (invasive) reading blood pressure apparatus. Other teachings include U.S. Pat. No. 4,372,148 which teaches a device that generates a variable frequency, variable pressure for use in a blood pressure measuring system to test the system for the presence of resonance or damping distortion so that a practioner can attribute any actual observations of such phenomena to the patient and not to the equipment. Other related apparatus concern test systems for blood pressure measuring equipment includes the teachings of U.S. Pat. Nos. 4,342,218, 4,269,058 and U.S. Pat. No. 2,556,043. Prior art relating to mock human appendages primarily for use as training aids in intravenous therapy includes U.S. Pat. Nos. 2,995,832 and 4,182,054.

The known systems are deemed inadequate to readily verify and calibrate the measurement performance of either invasive or noninvasive blood pressure measuring equipment. The present known systems do not include means for controlling the waveform of a stream of air under pressure from dedicated diastolic and systolic pressure regulators coupled to a source of air under pressure. The prior art systems known for verifying and calibrating blood pressure measuring equipment have not been provided with particular mock human appendages that are cuffed to non-invasive blood pressure measuring equipment. The prior art test systems have not been provided with control means for simulating an arterial blood pressure waveform and a dampening means to compensate for distortions that are attributable to the operation of the system.

Therefore, a need is believed to exist for apparatus and method for testing and verifying the accuracy of blood pressure measuring equipment. More particularly, a need is seen to exist for apparatus and method that tests and verifies the accuracy of non-invasive and invasive blood pressure measuring equipment. Even more particularly, a need is seen to exist for apparatus and method for testing and verifying the accuracy of blood pressure measuring equipment using pneumatic and electronic wave shaping equipment that simulate the delivery of systolic and diastolic blood pressures of a human to a mock human member or directly to a transducer member of an invasive blood pressure measuring unit.

SUMMARY OF THE INVENTION

Accordingly, the primary object of the present invention is to solve these deficiencies by providing a system that can verify and calibrate the measurement performance of either invasive or non-invasive blood pressure measuring equipment.

Another object of the present invention is to provide means for controlling the waveform of a stream of air under pressure from dedicated diastolic and systolic pressure regulators coupled to a source of air under pressure.

Another object of the present invention is to include with a system for verifying and calibrating blood pressure measuring equipment particular mock human appendages coupled to the test system and that can be cuffed to non-invasive blood pressure measuring equipment.

Still another object of the present invention is to provide the test system not only with a control means for simulating an arterial blood pressure waveform, but also, with dampening means to compensate for distortions in the supply of air pressure that are attributable to the operation of the system.

The present invention satisfies the foregoing objectives by providing a system tester arranged for testing invasive or noninvasive blood pressure measurement equipment. The system comprises of common components consisting of test monitoring equipment means that are coupled to pneumatic systolic and diastolic pressure generator means, which are controlled by electronic wave shaping equipment means and which pneumatic pressure generator means delivers a composite systolic and diastolic simulated human arterial blood pressure air stream, represented by SHW1 or SHW2, to a selected mock human appendage embodiment, in the case of testing non-invasive blood pressure measuring equipment, or directly to a transducer member of an invasive blood pressure measuring unit.

Therefore, to the accomplishments of the foregoing objects, the invention consists of the foregoing features hereinafter fully described and particularly pointed out in the claims, the accompanying drawings and following disclosure describing in detail the invention, such drawings and disclosure illustrating, however, but one of the various ways in which the invention may be practiced.

DESCRIPTION OF THE PREFERRED EMBODIMENT

A. SYSTEM OVERVIEW

Figure 1:
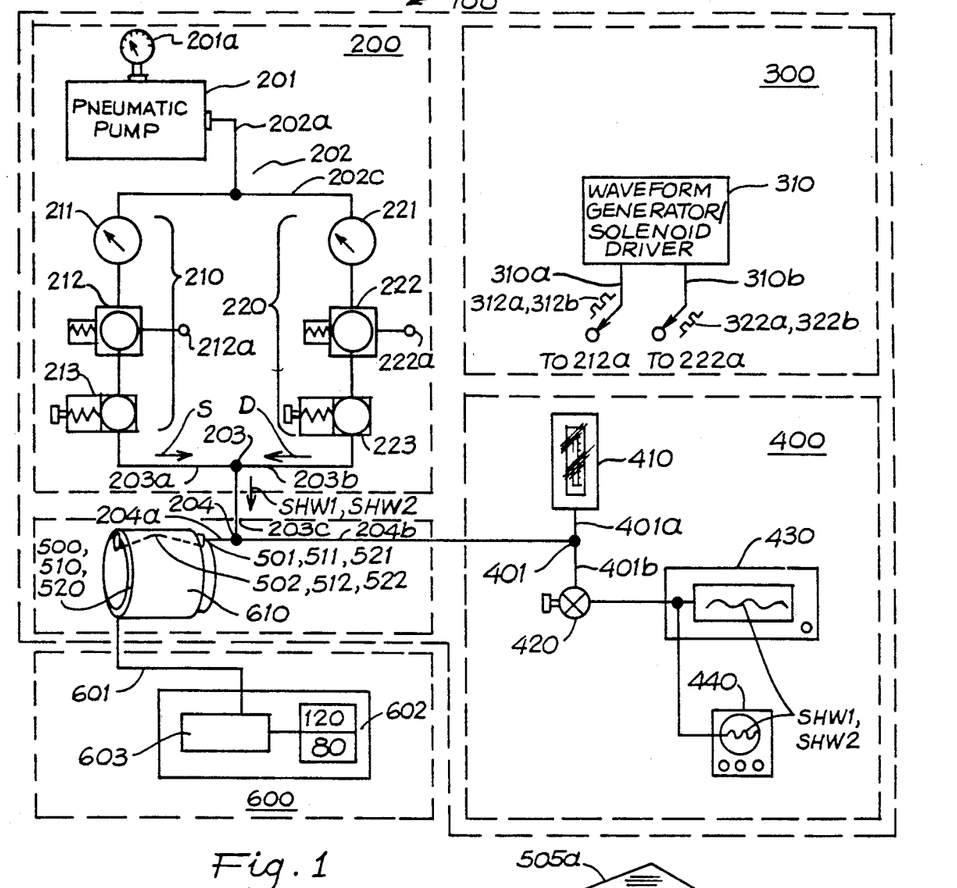
FIG. 1 is a block diagram of a system tester, according to the present invention, for testing non-invasive blood pressure measurement equipment, illustrating monitoring equipment coupled to a pneumatic member being controlled by electronic wave shaping equipment and delivering simulated systolic and diastolic pressures to a mock human member means.

FIG. 1 shows, in block diagram, a system tester 100 arranged for testing non-invasive blood pressure measurement equipment, shown generally as 600. The system 100 comprises test monitoring equipment means 400 coupled to pneumatic systolic and diastolic pressure generator means 200 which is being controlled by electronic wave shaping equipment means 300 and which pneumatic pressure generator means 200 is pneumatically delivering a composite systolic and diastolic simulated human arterial blood pressure, represented by SHW1 or SHW2, (depending upon whether wave shaping equipment 300 is driving solenoids 212/222 according to drive waveforms 312a, 322b or 321b, 322b, see FIGS. 2 and 6 respectively), to a selected one of mock human member pressure pulsating means, comprising embodiments 500, 510 or 520.

Figure 6:
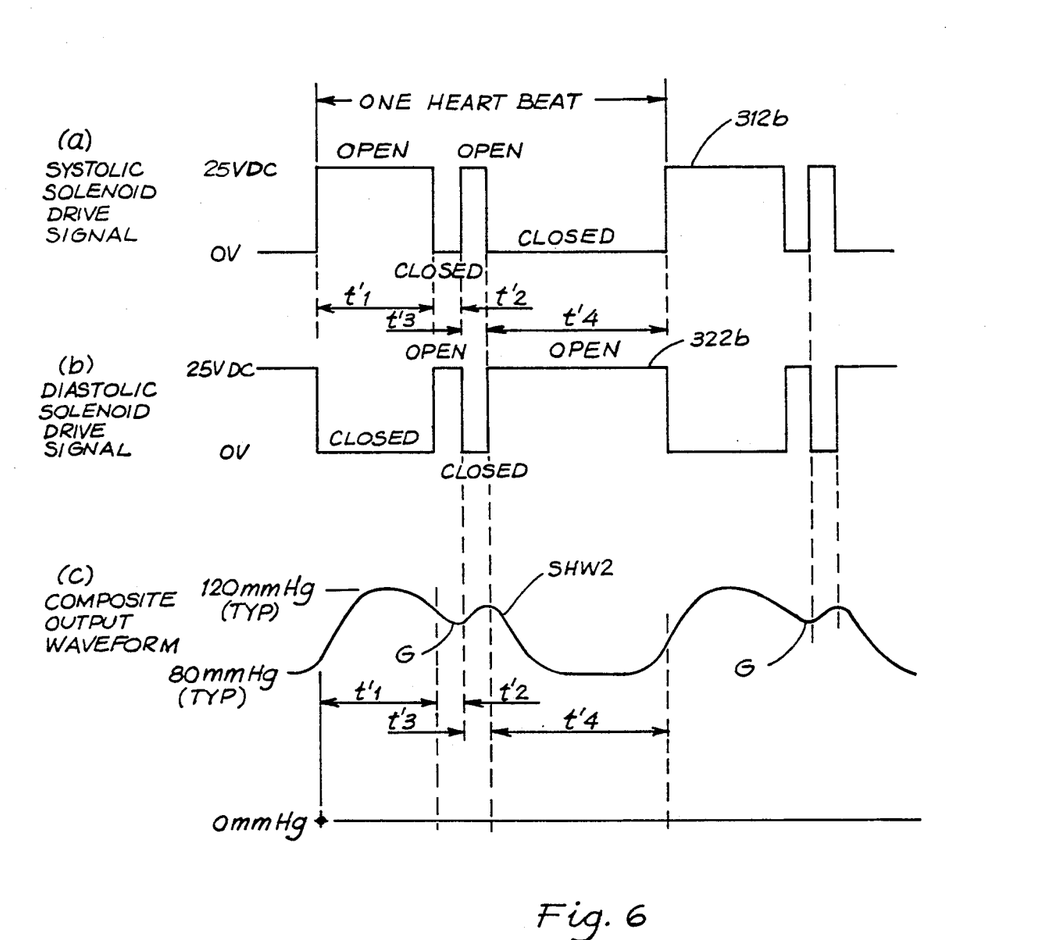
FIG. 6 illustrates, in three parts labeled (a), (b) and (c), improved control signals that better approximate the illustrated human arterial blood pressure measurement waveform shown in FIG. 2 (c), illustrating, respectively, the systolic simulated pressure, the diastolic simulated pressure and the composite output pressure waveform.
Figure 7:
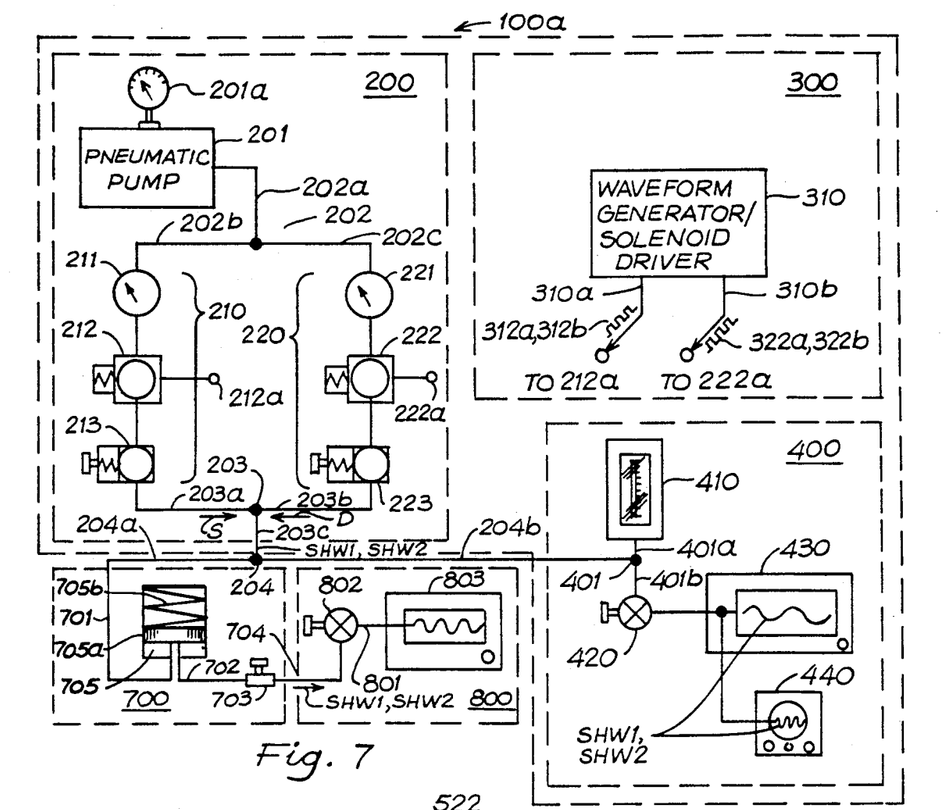
FIG. 7. is a block diagram of a system tester, according to the present invention, for testing invasive blood pressure measurement equipment, illustrating monitoring equipment coupled to a pneumatic member being controlled by electronic wave shaping equipment and delivering simulated systolic and diastolic pressures to a supplemental pneumatic wave dampening member and to the invasive blood pressure measurement equipment.

Similarly, FIG. 7 shows, in block diagram, system tester 100a testing an invasive blood pressure measurement equipment means 800. System 100a comprises the same blood pressure pulse simulating equipment as in FIG. 1, including test monitoring equipment means 400 coupled to pneumatic systolic and diastolic pressure generator means 200 which is being controlled by electronic wave shaping equipment means 300 and which pneumatic pressure generator means 200 is delivering a composite systolic and diastolic simulated human arterial blood pressure, represented by SHW1 or SHW2, see FIGS. 2 and 6 respectively, to the invasive blood pressure measurement equipment 800 after being dampened by supplemental pneumatic wave dampening member 700.

As will be explained below, delivery of pressure waveforms SHW1 or SHW2 depends upon whether wave shaping equipment 300 is driving solenoids 212/222 according to drive waveforms 312a, 322a or 312b, 322b.

B. COMMON ELEMENTS OF THE INVENTION

Referring back to FIG. 1 and also to FIG. 7, pneumatic systolic and diastolic pressure generator means 200 is shown comprising a pneumatic pump 201 having a pressure gauge 201a and output means 202 comprising a T-coupled arrangement consisting of tubing 202a feeding tubing 202b towards systolic pressure drive section 210 and also feeding tubing 202c towards diastolic pressure drive section 220. Systolic pressure drive section 210 comprises a systolic pressure regulator 211 feeding a controlled systolic solenoid valve 212 that feeds a systolic dampening valve 213. Controlled systolic solenoid valve 212 is provided with input terminal means 212a for receiving systolic solenoid drive output signal 312a or 312b from output 310a of waveform generator/solenoid driver 310 to produce pneumatic systolic pressure output S. Still referring to both FIGS. 1 and 7, and similarly as described above, diastolic pressure drive section 220 comprises a diastolic pressure regulator 221 feeding a controlled diastolic solenoid valve 222 that feeds a diastolic dampening valve 223. Controlled diastolic solenoid valve 222 is provided with input terminal means 222a for receiving diastolic solenoid drive output signal 322a or 322b from output 310b of waveform generator/solenoid driver 310 to produce pneumatic diastolic pressure output D. The outputs from the systolic pressure drive section 210 and the diastolic drive section 220 are joined at junction 203 by means of tubing 203a and 203b, respectively. The composite pneumatic output, be it SHW1 or SHW2, is delivered to a second junction 204 via tubing section 203c. From junction 204 the accuracy of the pneumatic waveforms SHW1 or SHW2 are checked by test monitoring equipment means 400 by coupling a probe tubing 204b to junction 401 that feeds a pressure gauge 410, via tubing 401a, and that also feeds transducer 420, via tubing 401b that drives strip chart recorder 430 and oscilloscope 440. Both strip chart recorder 430 and oscilloscope 440 record the pneumatic pressures SHW1 or SHW2 being delivered to a mock human member, 500, 510 or 520, as illustrated in FIG. 1 or to the invasive blood pressure equipment testing arrangement 700 and 800, as illustrated in FIG. 7.

C. NON-INVASIVE BLOOD PRESSURE EQUIPMENT TESTING MEANS

Up to now the description for the arrangements 100 or 100a for testing and verifying the accuracy of non-invasive or the invasive blood pressure measuring equipment has been the same. The departure obviously concerns the type of equipment being tested. The description of arrangement 100 for non-invasive blood pressure measuring equipment 600 requires the use of a means to simulate a human appendage that normally is cuffed to obtain systolic and diastolic blood pressure readings. For this purpose the appendage members 500, 510 or 520 are presented. Regardless of embodiment, tubing 204a provides the pneumatic input to the respective appendage member input, 501, 511 or 521.

Figure 3:
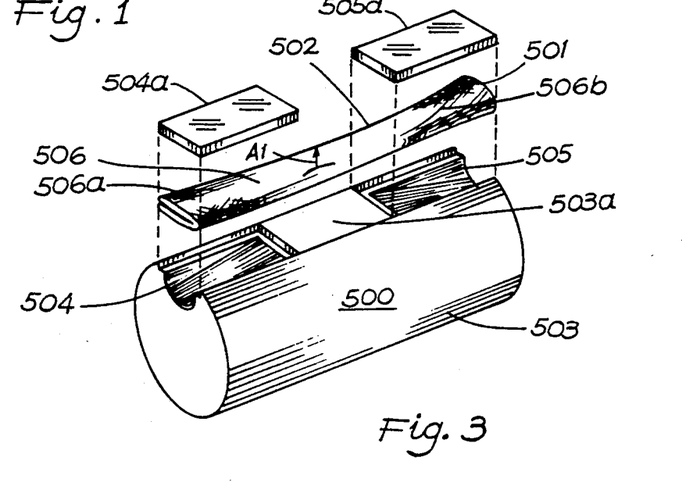
FIGS. 3, 4 and 5 illustrate three embodiments of mock human appendage members, including, respectively, a first mock arm, a second mock arm and a mock finger that are adapted to exhibit blood pressure pulses and for attachment to the probe member of blood pressure measurement equipment.

For example, the mock human arm 500 illustrated in FIG. 3 comprises a thin walled resilient tubing 506 having an input side 501 and a closed terminating end 506a. The tubing 506 is disposed on an elongated solid cylindrical member 503 made of a material, such as rubber, that resembles the texture of a human arm. The tubing 506 is longitudinally disposed having ends 506a and 506b disposed on grooves 504 and 505, respectively. Ends 506a and 506b are secured in grooves 504 and 505 by caps 504a and 505a, respectively. Tubing 506 has mid portion 502 that will be disposed on wall portion 503a. Tubing 506, upon being disposed as described, will be sufficiently relaxed to enable mid portion 502 to pulsate as indicated by arrow A1 in accordance with the pneumatic pressure changes of input pressure waveforms SHW1 or SHW2 being received at input portion 501. As illustrated in FIG. 1, cuff member 610, encircling mock arm embodiment 500 at mid portion 502, senses and transmits the pulsations due to pressure changes via probe line 601 to the transducer portion 603 which drives a display 602 that displays the diastolic and systolic readings. The readings displayed on display 602 are compared to the readings at strip chart 430, at oscilloscope 440, and at the respective regulators gauges 211 and 221 for the systolic and diastolic pressure readings to verify performance of the non-invasive blood pressure measuring equipment 600.

Figure 5:
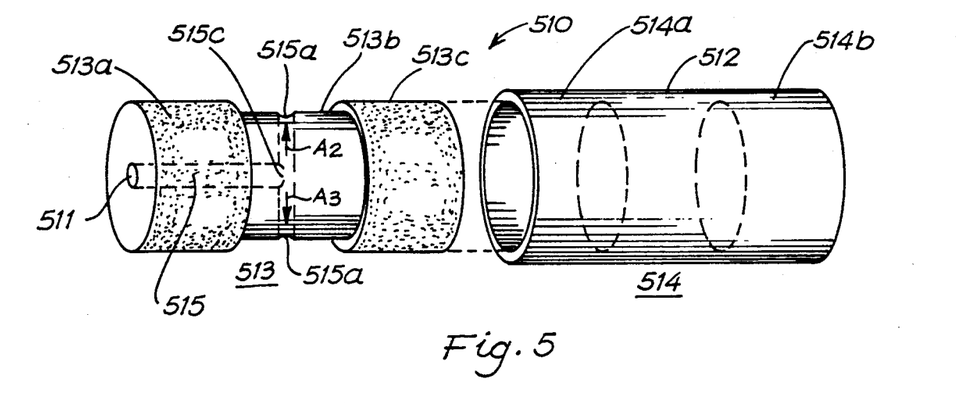

Alternatively, a mock human finger member 510, comprised of inner section 513 and outer section 514, may be utilized to check equipment 600. The mock finger inner section 513 is adapted with a tube portion 515 having an input end 511 that may receive pneumatic input from tubing section 204a. Tube portion 515 terminates at a chamber 515c having outlets 515a that enables pneumatic air pressure to exit as indicated by arrows A2 and A3. Inner section 513 is intended to be mated with outer section 514 to provide a sealed enclosure 513b beneath portion 512. The sealed enclosure is provided by having ends 513a and 513c in a closely coupled air-tight relationship with outer portion 514a and 514b, respectfully. The wall thickness and choice material of outer portion 514, and especially portion 512, is chosen to enable flexing due to the force exerted by the pulsating pressure of pneumatic air pressure waveforms SHW1 or SHW2, as indicated by arrows A2 and A3. As when using the embodiment 500, the outer portion 512 will be encircled by cuff member 610 which senses and transmits the pulsations due to pressure changes to the unit under test and calibration.

Figure 4:
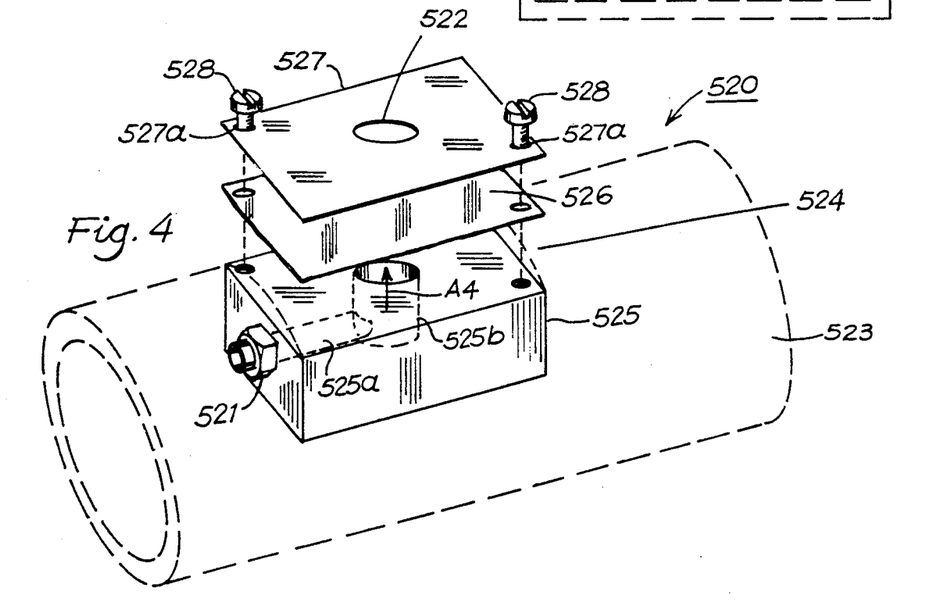

Another embodiment of a mock human arm member is shown as member 520 in FIG. 4. In this embodiment, an elongated solid cylindrical member 523 made of a material, such as rubber, that resembles the texture of a human arm, encloses a chamber member 524 that provides means for externally exhibiting pneumatic air pressure changes in accordance with air pressure waveforms SHW1 or SHW2. Chamber 524 comprises an enclosure 525, a membrane 526 and an external plate 527. Enclosure 525 is provided with a tubing 525a having an input end 521 and an outlet end terminating at a hollow chamber portion 525b. Membrane 526, with the aid of plate 527 and associated hardware 528 fitting through mounting holes 527a, is disposed over enclosure 525 to provide an air-tight seal of chamber portion 525b. Plate 527 is provided with an opening 522 for enabling a portion of membrane 526 that is directly under opening 522 to flex in response to air pressure changes within chamber portions 525b as indicated by arrow A4 and in accordance with air pressure waveforms SHW1 or SHW2. As when using the embodiments 500 or 510, the plate 527, and in particular opening 522 will be encircled by cuff member 610 which senses and transmits the pulsations due to pressure changes to the unit under test and calibration.

D. OPERATION OF THE TEST SYSTEM

In operation, waveform generator/solenoid driver 310 is programmed to deliver from output 310a to input terminal means 212a either control signal drive waveforms 312a or 312b depending upon how closely the simulation of the human arterial blood pressure HW is desired. Similarly, waveform generator/solenoid driver 310 is programmed to deliver from output 310b to input terminal means 222a either control signal drive waveforms 322a or 322b depending upon how closely the simulation of the human arterial blood pressure HW is desired. By comparing composites SHW1 and SHW2 with HW in FIGS. 2 (c) and 6 (c), SHW2 is seen to be a closer simulation of HW.

Figure 2:
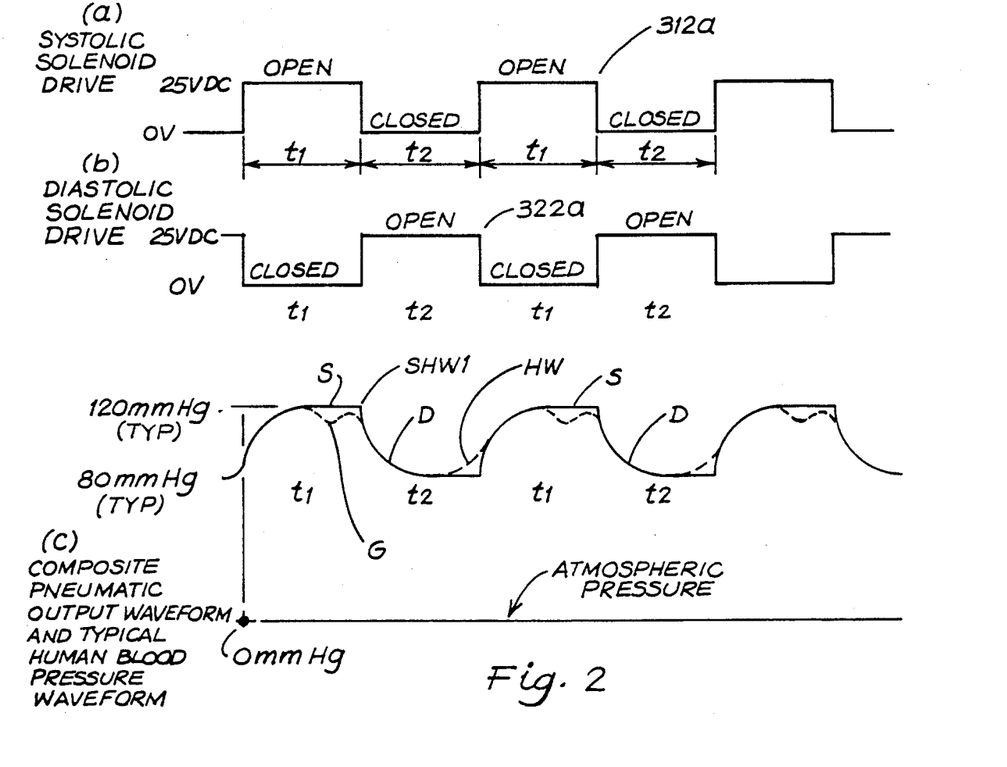
FIG. 2 illustrates, in three parts labeled (a), (b) and (c), the control signals for controlling: the systolic simulated pressure, the diastolic simulated pressure and the composite pressure waveform superimposed over a graphically illustrated human arterial blood pressure measurement waveform, respectively.

When delivering pneumatic air pressure in accordance with waveform SHW1 and as seen from FIG. 2 (c), HW is periodic as shown by periodic time intervals t1 and t2. Generator 310 is programmed for a time interval t to provide periodic electrical output signals 312a and 322a that simulate the periodic nature of HW by electrically energizing solenoid valves 212 and 222 according to the magnitude of the voltage of output signals 312a or 322a. By example, when output 322a is at 0 volts (V) the diastolic solenoid 222 is not energized, however, since output 312a is programmed to concurrently be at 25 VDC, solenoid valve 212 is energized which allows the passage of systolic pneumatic air pressure S which is maintained by systolic pressure regulator 211 at 120 mm Hg. Similarly, when output 312a is at 0 volts (V) the systolic solenoid 212 is not energized, and since output 322a is at 25 VDC solenoid valve 222 is energized and allows the passage of diastolic pneumatic air pressure D which is maintained by diastolic pressure regulator 211 at 80 mm Hg. The result of periodically energizing solenoids 212 and 222 produces the composite waveform SHW1 which is delivered to the unit under test, i.e. non-invasive blood pressure measuring equipment 600 or invasive blood pressure measuring equipment 800.

The pressure waveform SHW1 is a close simulation of the target human systolic and diastolic blood pressure waveform HW. However, SHW1 does not simulate the dip G seen in waveform HW which is a commonly observed dip in blood pressure measurements of humans and which has been desirable to simulate. The waveform SHW2, illustrated in FIG. 6 (c) is a simulated version of HW with dip G that more closely resembles HW than SHW1. To produce SHW2, solenoid control signal waveforms 312b and 322b, shown in FIG. 6 (a) and (b), are programmed into generator 310 to be delivered to valve solenoids 212 and 222 from outputs 310a and 310b. As shown in FIG. 6 (c), during time interval t'1, solenoid 212 is energized and SHW2 is at its peak air pressure. When solenoid 212 is deenergized and solenoid 222 is energized, the air pressure of SHW2 is reduced towards the lower pressure of 80 mm Hg for a time interval t'2. However, before the lower pressure is reached, solenoid 222 is de-energized and solenoid 212 is energized and enables air pressure of SHW2 to increase towards the 120 mm Hg for a time interval of t'3. After time interval t'3, the diastolic solenoid 222 is again energized and the systolic solenoid is deenergized to reduce the air pressure to 80 mm Hg for a time interval of t'4, after which time the periodic control of solenoids 212 and 222 is repeated to produce a continuous pressure waveform SHW2 that more closely simulates HW than waveform SHW1.

In using an air pressure waveform SHW2, it may be desirable to smooth the turbulance caused by the rapid opening and closing of solenoids 212 and 222. To accomplish smoothing the stream of air pressure being delivered to a unit under test, a supplemental pneumatic wave dampening member 700 is located in-line with output 204a and the unit under test, as shown by example in FIG. 7, when testing an invasive blood pressure measuring equipment 800. By referring to FIG. 7, damper member 700 is seen to comprise an input section 701 that is common with output 204a and that feeds to a damper chamber 705 having dampening elements such as a piston 705a and spring 705b. The dampened air stream exits damper chamber 705 via tubing 702 and continues via a shut-off valve 703 and tubing 704 that connects to the inlet side of transducer 802 of equipment 800. The display portion 803 is connected to transducer 802 via interconnecting means 801 that relays corresponding signals of the air pressure changes being received.

Therefore, while the present invention has been shown and described herein in what is believed to be the most practical and preferred embodiments, it is recognized that departures can be made therefore within the scope of the invention, which is therefore not to be limited to the details disclosed therein but is to be accorded the full scope of the claims so as to embrace any and all equivalent apparatus.

We claim:

1. Apparatus for testing and verifying the accuracy of blood pressure measuring equipment, said apparatus comprising:

fluid pressure generating means for producing simulated human systolic and diastolic blood pressures;

electronic means electrically coupled to said fluid pressure generating means for delivering control signals that enable delivery of said simulated human systolic and diastolic blood pressures; and interface means for transferring said simulated human systolic and diastolic blood pressures from said fluid pressure generating means to said blood pressure measuring equipment, said fluid pressure generating means comprising:

pneumatic pump means for providing a continuous stream of pressurized air, a first pressure regulated line pneumatically coupled to said pneumatic pump means, and a second pressure regulated line pneumatically coupled to said pneumatic pump means, said first and second pressure regulated lines carrying pressurized air at pressures corresponding to simulated human systolic and diastolic arterial blood pressures, respectively.

2. Apparatus for testing and verifying the accuracy of blood pressure measuring equipment as recited in claim 1, further including:

monitor means for displaying pneumatic pressure information.

3. Apparatus for testing and verifying the accuracy of blood pressure measuring equipment as recited in claim 1, wherein:

said electronic means comprises a first and a second signal output means for delivering respective first and second periodic control signals to said pneumatic means that collectively emulate a periodic human arterial blood pressure cycle, said first periodic control signal emulating a systolic pressure waveform having a preselected systolic pressure amplitude and period and said second periodic control signal emulating a diastolic pressure waveform of a preselected diastolic pressure amplitude and period.

4. Apparatus for testing and verifying the accuracy of blood pressure measuring equipment as recited in claim 1, wherein:

said interface means comprises mock human appendage means for transferring said simulated human systolic and diastolic blood pressures from said fluid pressure generating means to a non-invasive type of blood pressure measuring equipment.

5. Apparatus for testing and verifying the accuracy of blood pressure measuring equipment as recited in claim 4, wherein:

said mock human appendage means comprises a thin walled tubing having an input end and a closed terminating end, said tubing being disposed on an elongated solid cylindrical member made of a rubber-like material that resembles a human arm, said tubing being longitudinally disposed on said elongated solid cylindrical member and having said input and terminating ends disposed on grooves and being secured in said grooves with respective caps, said tubing having a mid portion exposed on a surface portion of said elongated solid cylindrical member for exhibiting pulsations from said delivery of said simulated human systolic and diastolic blood pressures, and for being cuffed to a cuff member of said noninvasive type of blood pressure measuring equipment to effect said transfer of said simulated human systolic and diastolic blood pressures from said fluid pressure generating means.

6. Apparatus for testing and verifying the accuracy of blood pressure measuring equipment as recited in claim 4, wherein:

said mock human appendage means comprises a mock human finger having an inner section and an outer section, said inner section provided with a tube portion having an input end for pneumatically coupling to said pneumatic means, said tube portion terminating at a chamber portion of said inner section and having outlet means for enabling pneumatic pressure to exit, said inner section mating with said outer section to create an air-tight enclosure portion about said chamber portion, said outer portion having a thin wall thickness that enables flexing upon delivery of said simulated human systolic and diastolic blood pressures, and for being cuffed to a cuff member of said non-invasive type of blood pressure measuring equipment to effect said transfer of said simulated human systolic and diastolic blood pressures from said fluid pressure generating means.

7. Apparatus for testing and verifying the accuracy of blood pressure measuring equipment as recited in claim 4, wherein:

said mock human appendage means comprises a mock human arm including an elongated solid cylindrical member made of a rubberlike material that resembles the texture of a human arm, said solid cylindrical member enclosing a chamber member comprising an enclosure, a membrane and an external plate, said enclosure provided with a tubing having an input end and an outlet end, said outlet end terminating at a hollow inner chamber portion, said membrane being disposed over said enclosure and providing an airtight seal of said inner chamber portion, said external plate having an opening for enabling a portion of said membrane that is directly over said opening to flex in response to delivery of said simulated human systolic and diastolic blood pressures, and for being cuffed to a cuff member of said non-invasive type of blood pressure measuring equipment to effect said transfer of said simulated human systolic and diastolic blood pressures from said fluid pressure generating means.

8. Apparatus for testing and verifying the accuracy of blood pressure measuring equipment as recited in claim 1, wherein:
said interface means comprises a pneumatic dampening member located in-line with an output line from said fluid pressure generating means and an invasive type blood pressure measuring equipment under test.

9. Apparatus for testing and verifying the accuracy of blood pressure measuring equipment, said apparatus comprising:
fluid pressure generating means for producing simulated human systolic and diastolic blood pressures;
electronic means electrically coupled to said fluid pressure generating means for delivering control signals that enable delivery of said simulated human systolic and diastolic blood pressures; and
interface means for transferring said simulated human systolic and diastolic blood pressures from said fluid pressure generating means to said blood pressure measuring equipment, said fluid pressure generating means comprising:
(a) a pneumatic pump means for providing a continuous stream of pressurized air,
(b) a first pressure regulated line pneumatically coupled to said pneumatic pump means, said first pressure regulated line including a first adjustable air pressure regulator for maintaining said stream of air at a preselected systolic pressure value, and a first solenoid valve pneumatically coupled to said first adjustable air pressure regulator and electrically coupled to said electronic means, said first solenoid valve receiving a first control signal from said electronic means that actuates said first solenoid valve and that determines periodic delivery of said stream of air at said preselected systolic pressure value, and
(c) a second pressure regulated line pneumatically coupled to said pneumatic pump means, said second pressure regulated line including a second adjustable air pressure regulator for maintaining said stream of air at a preselected diastolic pressure value, a second solenoid valve pneumatically coupled to said second adjustable air pressure regulator and electrically coupled to said electronic means, said second solenoid valve receiving a second control signal from said electronic means that actuates said second solenoid valve and that determine periodic delivery of said stream of air at said preselected diastolic pressure value.

10. Apparatus for testing and verifying the accuracy of blood pressure measuring equipment as recited in claim 9, wherein:
said first pressure regulated line further includes a first dampening means pneumatically coupled to said first solenoid valve for receiving said periodic delivery of said stream of air at said preselected systolic pressure value, said dampening means smoothing air turbulances caused by said first control signal actuating said first solenoid valve and producing a smooth simulated systolic blood pressure output component; and
said second pressure regulated line further includes a second dampening means pneumatically coupled to said second solenoid valve for receiving said periodic delivery of said stream of air at said preselected diastolic pressure value, said dampening means smoothing air turbulances caused by said control signal actuating said second solenoid valve and producing a smooth simulated diastolic blood pressure output component.

11. Apparatus for testing and verifying the accuracy of blood pressure measuring equipment, said apparatus comprising:
fluid pressure generating means for producing simulated human systolic and diastolic blood pressures;
electronic means electrically coupled to said fluid pressure generating means for delivering control signals that enable delivery of said simulated human systolic and diastolic blood pressures; and
interface means for transferring said simulated human systolic and diastolic blood pressures from said fluid pressure generating means to said blood pressure measuring equipment, said interface means comprising mock human appendage means for transferring said simulated human systolic and diastolic blood pressures from said fluid pressure generating means to a non-invasive type of blood pressure measuring equipment, said fluid pressure generating means comprising:
(a) pneumatic pump means for providing a continuous stream of pressurized air,
(b) a first pressure regulated line pneumatically coupled to said pneumatic pump means, said first pressure regulated line including a first adjustable air pressure regulator for maintaining said stream of air at a preselected systolic pressure value, and a first solenoid valve pneumatically coupled to said first adjustable air pressure regulator and electrically coupled to said electronic means, said first solenoid valve receiving a first control signal from said electronic means that actuates said first solenoid valve and that determines periodic delivery of said stream of air at said preselected systolic pressure value and
(c) a second pressure regulated line pneumatically coupled to said pneumatic pump means, said second pressure regulated line including a second adjustable air pressure regulator for maintaining said stream of air at a preselected diastolic pressure value, a second solenoid valve pneumatically coupled to said second adjustable air pressure regulator and electrically coupled to said electronic means, said second solenoid valve receiving a second control signal from said electronic means that actuates said second solenoid valve and that determine periodic delivery of said stream of air at said preselected diastolic pressure value.

12. Apparatus for testing and verifying the accuracy of blood pressure measuring equipment as recited in claim 11, wherein:
said first pressure regulated line further includes a first dampening means pneumatically coupled to said first solenoid valve for receiving said periodic delivery of said stream of air at said preselected systolic pressure value, said dampening means smoothing air turbulances caused by said first control signal actuating said first solenoid valve and producing a smooth simulated systolic blood pressure output component; and said second pressure regulated line further includes a second dampening means pneumatically coupled to said second solenoid valve for receiving said periodic delivery of said stream of air at said preselected diastolic pressure value, said dampening means smoothing air turbulances caused by said control signal actuating said second solenoid valve and producing a smooth simulated diastolic blood pressure output component.

13. Apparatus for testing and verifying the accuracy of blood pressure measuring equipment as recited in claim 11, wherein:

said electronic means comprises a first and a second signal output means for delivering respective first and second periodic control signals to said pneumatic means that collectively emulate a periodic human arterial blood pressure cycle, said first periodic control signal emulating a systolic pressure waveform having a preselected systolic pressure amplitude and period and said second periodic control signal emulating a diastolic pressure waveform of a preselected diastolic pressure amplitude and period.

* * * * *